US009642565B2

United States Patent
Gonopolskiy et al.

(10) Patent No.: US 9,642,565 B2
(45) Date of Patent: May 9, 2017

(54) DEFORMABLE PHYSIOLOGICAL SENSOR

(75) Inventors: Oleg Gonopolskiy, West Bloomfield, MI (US); Rick Scheuing, Rochester Hills, MI (US)

(73) Assignee: Covidien LP, Mansfield, MA (US)

( * ) Notice: Subject to any disclaimer, the term of this patent is extended or adjusted under 35 U.S.C. 154(b) by 1886 days.

(21) Appl. No.: 12/163,181

(22) Filed: Jun. 27, 2008

(65) Prior Publication Data
US 2009/0012380 A1    Jan. 8, 2009

Related U.S. Application Data

(60) Provisional application No. 60/946,607, filed on Jun. 27, 2007.

(51) Int. Cl.
*A61B 5/1455* (2006.01)
*A61B 5/00* (2006.01)

(52) U.S. Cl.
CPC ........ *A61B 5/14552* (2013.01); *A61B 5/0059* (2013.01); *A61B 5/14553* (2013.01); *A61B 2562/085* (2013.01); *A61B 2562/164* (2013.01)

(58) Field of Classification Search
CPC ............ A61B 5/14551; A61B 5/14552; A61B 5/14553; A61B 5/6832; A61B 5/6833; A61B 2562/164; A61B 2562/166

USPC ........ 600/309, 310, 322, 323, 344; 606/2, 9, 606/13
See application file for complete search history.

(56) References Cited

U.S. PATENT DOCUMENTS

| | | | | |
|---|---|---|---|---|
| 5,584,296 | A | * | 12/1996 | Cui et al. ...................... 600/479 |
| 5,879,373 | A | * | 3/1999 | Roper et al. .................. 600/344 |
| 7,190,986 | B1 | * | 3/2007 | Hannula et al. .............. 600/344 |
| 7,706,853 | B2 | * | 4/2010 | Hacker et al. ................ 600/344 |
| RE41,317 | E | * | 5/2010 | Parker .......................... 600/344 |
| RE43,169 | E | * | 2/2012 | Parker .......................... 600/344 |
| RE43,860 | E | * | 12/2012 | Parker .......................... 600/344 |
| 2001/0031916 | A1 | * | 10/2001 | Bennett et al. ............... 600/383 |
| 2002/0165440 | A1 | * | 11/2002 | Mason et al. ................. 600/344 |
| 2006/0173247 | A1 | * | 8/2006 | Medina ............. A61B 5/14552 600/301 |
| 2007/0123756 | A1 | * | 5/2007 | Kitajima et al. ............. 600/300 |
| 2008/0076996 | A1 | * | 3/2008 | Hoarau ......................... 600/344 |

FOREIGN PATENT DOCUMENTS

WO    WO 0059374 A1 * 10/2000

* cited by examiner

*Primary Examiner* — Adam J Eiseman
(74) *Attorney, Agent, or Firm* — Harness, Dickey & Pierce PLC

(57) ABSTRACT

A sensor for measuring physiological characteristics is provided that includes a circuit assembly and a means of deforming the sensor to a desired shape of small radius compound curvature. In one embodiment, the sensor includes a deformable layer configured to conform and maintain a shape of a surface on which the sensor is applied.

24 Claims, 6 Drawing Sheets

DEFORMABLE PHYSIOLOGICAL SENSOR

CROSS REFERENCE TO RELATED APPLICATIONS

This application is a non-provisional application claiming priority to U.S. Ser. No. 60/946,607, with a filing date of Jun. 27, 2007, which application is hereby incorporated by reference in its entirety.

BACKGROUND

Physiological sensor systems are used to measure a variety of physiological characteristics such as blood metabolite and oxygen saturation in body tissues using multiple wavelengths of light. Physiological sensor systems generally include a monitoring system connected to a sensor pad that adheres to the portion of the body being tested. The sensor pad includes a plurality of optical components that generally protrude through the outer surface of the sensor pad. The thickness and configuration of the optical components on the pad often generate pressure points when external force or pressure is applied. These pressure points can be painful and damaging to sensitive skin, particularly in neonates when the sensor pad is secured to the body by a head band, cap or other means.

Accordingly, the embodiments described hereinafter were developed in light of these and other drawbacks associated with existing physiological sensor pads.

DETAILED DESCRIPTION

A physiological sensor assembly that adheres and conforms to small radius compound curvatures is provided. The sensor is a non-invasive, disposable sensor with a multi-layered structure that includes a flexcircuit assembly and a padding assembly having a top foam layer and a bottom foam layer. The flexcircuit assembly includes a plurality of optical components and is disposed along a mechanical neutral axis of the padding assembly with the optical components, being considerably thicker than the flexcircuit, protruding above and below the flexcircuit when viewed from the side to maximize flexibility. The sensor also includes a deformable layer configured to maintain a compound curvature shape once applied to a sensing surface.

Figure 1:
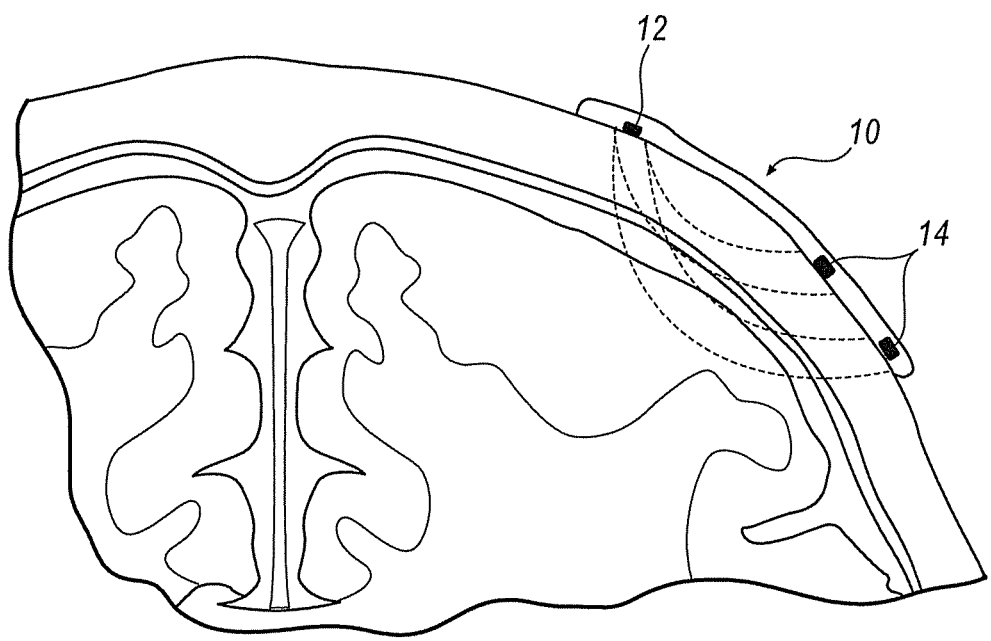
FIG. 1 illustrates an exemplary sensor pad assembly, according to an embodiment.

FIG. 1 illustrates an exemplary sensor pad assembly 10 as applied to a patient for measuring a physiological characteristic such as blood metabolite. The sensor 10 operates by emitting light of a plurality of near infrared wavelengths and measuring its transmitted and reflected intensities at a plurality of unequal distances from the emitter locations. This information is used to calculate blood metabolite and other physiological measurements. One of ordinary skill in the art understands that the sensor pad of FIG. 1 is exemplary in that it includes one light source 12 (i.e, emitters) and two detectors 14, one configured for shallow detection and one configured for deep detection. However, alternative embodiments may include a plurality of light sources 12 with any number of detectors 14 in any configuration. In addition, one of ordinary skill in the art understands that although there is one light source 12, each light source 12 may be capable of emitting multiple wavelengths of light 16.

Figure 2:
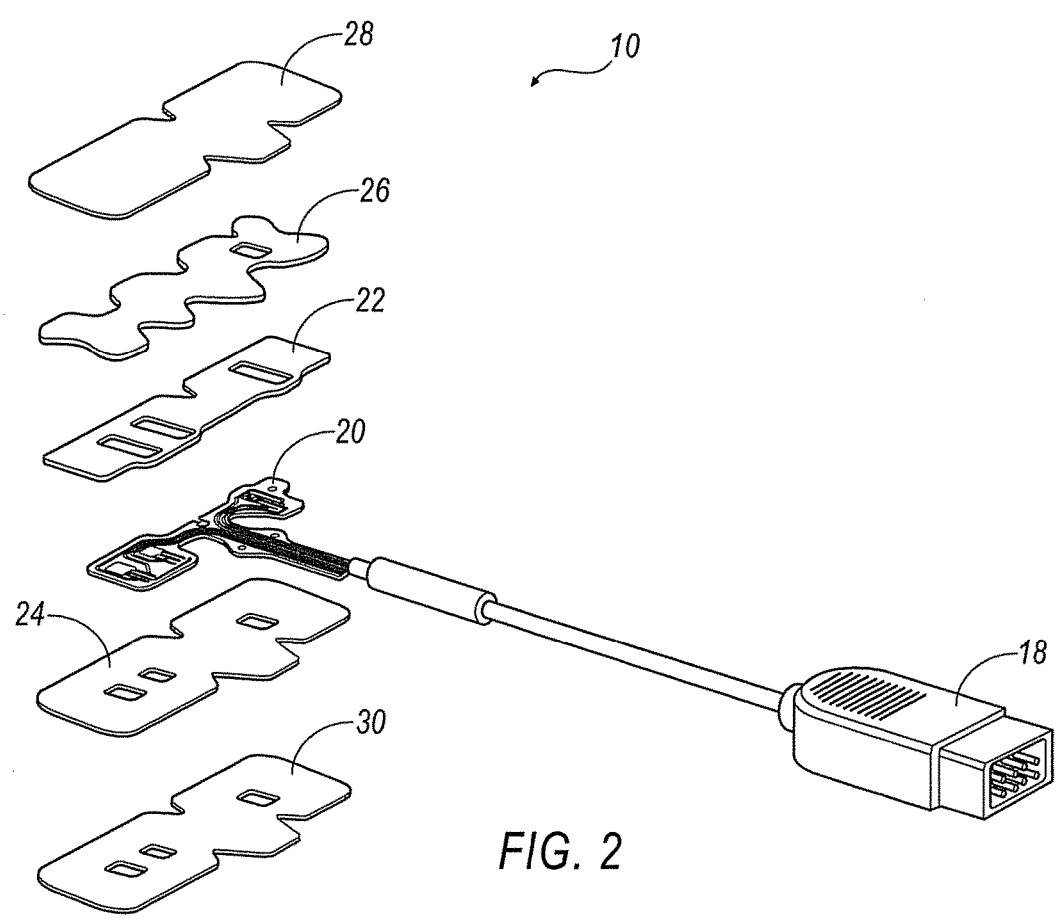
FIG. 2 illustrates an exploded view of an exemplary sensor pad assembly, according to an embodiment.

FIG. 2 illustrates an exploded view of an exemplary sensor pad assembly 10 having a cable assembly 18 connected to a flexcircuit assembly 20 disposed between a top foam layer 22 and a bottom foam layer 24. The sensor pad assembly 10 further includes a deformable layer 26, a top cover 28 and a patient adhesive layer 30. In one embodiment, the patient adhesive layer 30 includes a hydrocolloid adhesive, which is recommended by the National Association of Neonatal Nurses for skin application because it is less aggressive than the medical grade acrylic adhesive that is typically used on known physiological sensors. Hydrocolloid adhesive is generally used for wound care or as a buffer for other devices with more aggressive adhesives. The hydrocolloid adhesive allows the sensor pad to be easily applied to and removed from delicate patient skin.

The deformable layer shown in FIG. 2 is configured to conform to and maintain a compound curvature shape once the sensor is applied to the patient to minimize the chance of it peeling up over time. A compound curvature may include a variety of surface topologies, including but not limited to, small radius compound curvatures often encountered in neonatal patients. In one example, a small radius compound curvature could be characterized as the smallest compound curvature of a human head. Stated another way, a small radius compound curvature may reference the shape of a premature infant's head whose diameter may be as small as 5-6 cm (radius=2.5-3.0 cm). In other words, a surface with curvature in one direction is considered a cylinder, while a compound curvature in this case means that this radius exists in both directions, which would theoretically form a sphere. In general, maintaining the adhesion of a sensor to a cylinder is easier than conforming and maintaining the shape of a compound curvature such as a sphere.

In alternative embodiments, the deformable layer may also be used to reflect and intensify the emitted light. Maintaining shape could also be accomplished by using a flexcircuit of appropriate shape and sufficient metallization or other embodiments. The deformable layer 26 may be aluminum or any other material suitable for conforming to and maintaining its shape.

Figure 3:
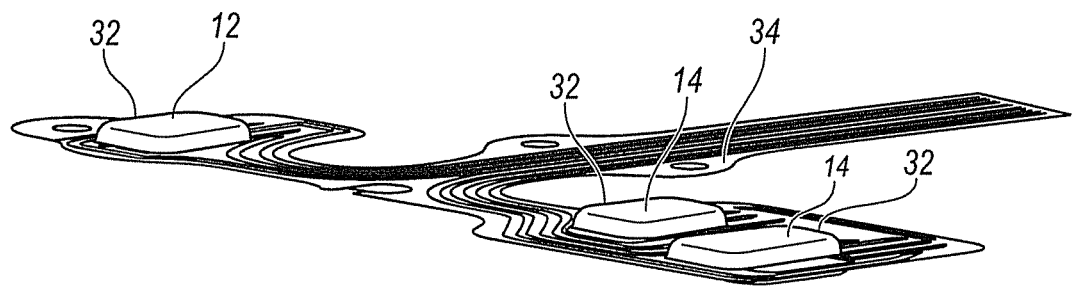
FIG. 3 illustrates a side view of an exemplary flexcircuit assembly, according to an embodiment.
Figure 4:
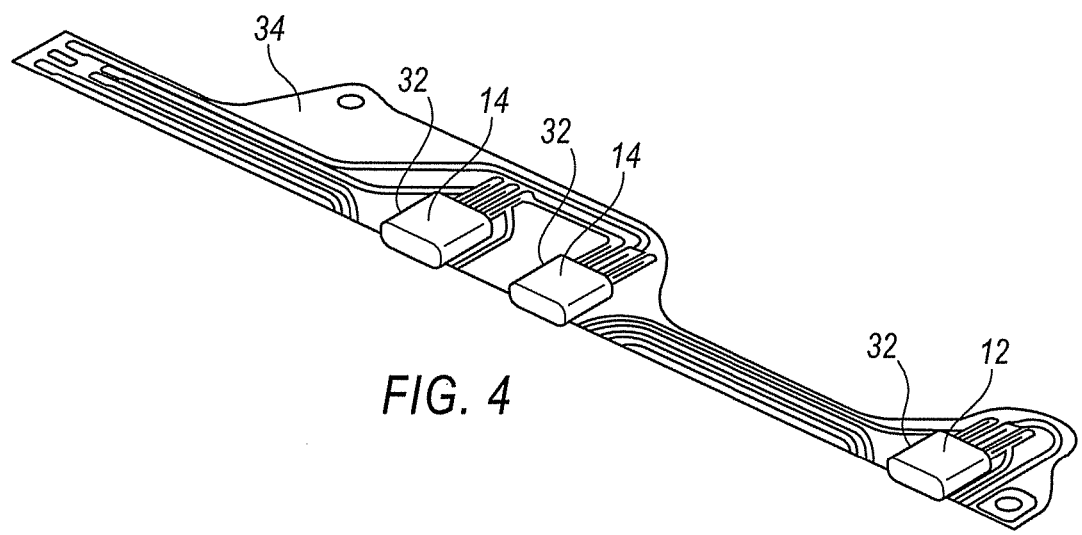
FIG. 4 illustrates another side view of an exemplary flexcircuit assembly, according to an embodiment.

As best shown in FIGS. 3-6, the flexcircuit assembly 20 includes a plurality of optical components 32 that are mounted to the flexcircuit 34 such that the horizontal plane of the flexcircuit 34 is axially aligned with the mechanical center of each of the optical components (See FIGS. 3-4). In this way, the padding materials 22, 24 (i.e., the top and bottom foam layers) when assembled on both the patient side and the opposite side of the flexcircuit 34 equal the thickness of the optical components 32, which minimizes potential pressure points generally caused by the optical component thickness. In one embodiment, the flexcircuit 34, optical components 32 and cable assembly 18 are procured as a subassembly and the optics and cable are soldered to the flexcircuit 34. Once the subassembly is tested and calibrated, the pad layers (i.e., the padding materials 22, 24 and the patient adhesive 30) are laminated on each side of the flexcircuit 34 to form the pad assembly according to the exploded view in FIG. 2. In one embodiment, the pad layer lamination is achieved using specific adhesives that are procured already laminated to each layer. The pad layers are made using laminating machines and die cutting or laser cutting tools.

In one embodiment, copper traces are used to provide electrical connectivity between flexcircuit components. In contrast to silver ink traces, which are generally used in some known sensor configurations, copper traces have a relatively high conductivity and can be narrower than silver ink. This allows the flexcircuit 34 to be considerably narrower to maximize its ability to conform to compound curvature.

Figure 5:
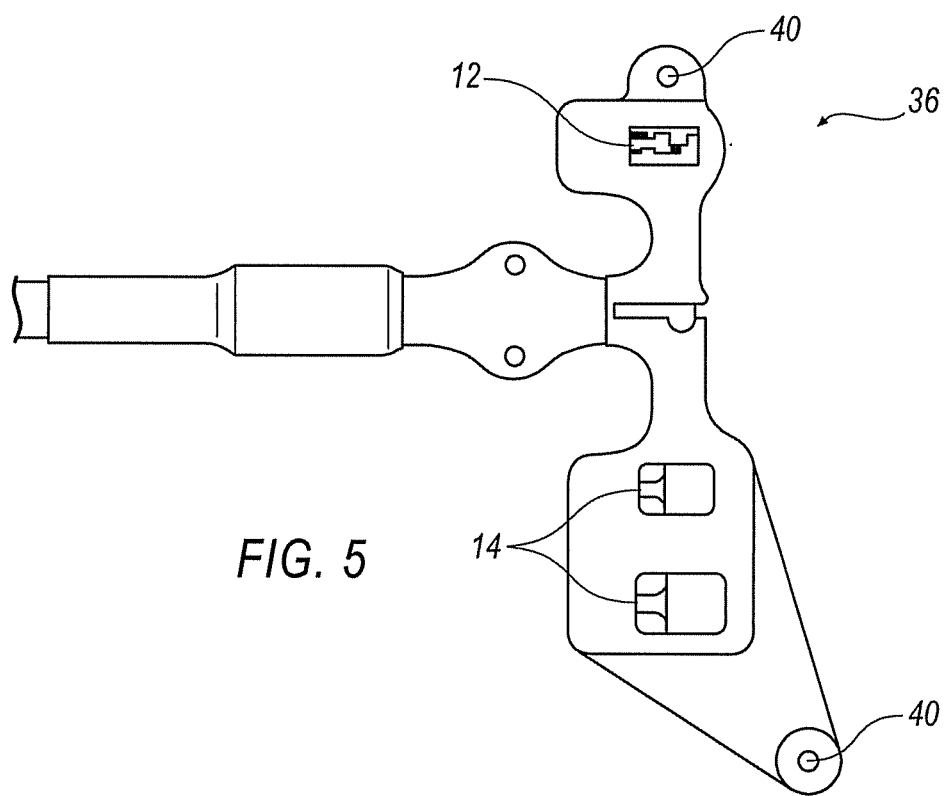
FIG. 5 illustrates a patient side view of an exemplary flexcircuit assembly, according to an embodiment.
Figure 6:
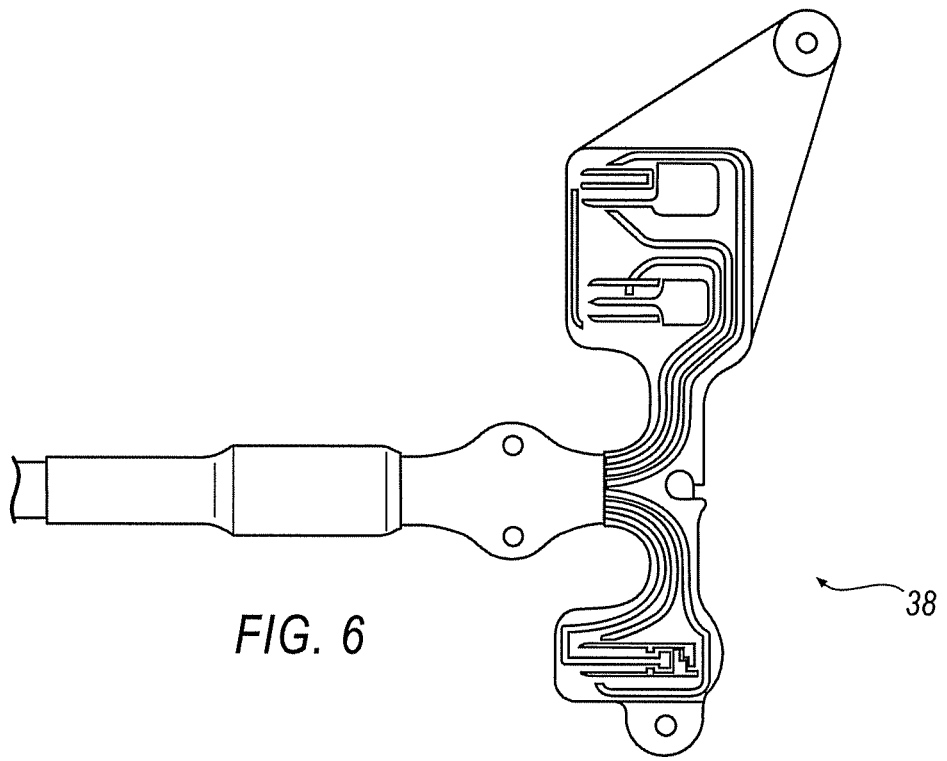
FIG. 6 illustrates a top side view of an exemplary flexcircuit assembly, according to an embodiment.

FIGS. 5 and 6 illustrate a patient side 36 and a top side 38, respectively, of an exemplary sensor pad assembly 10. In operation each physiological sensor is calibrated so that a monitor can normalize for differences in emitter brightness and detector sensitivity. The calibration data is stored on a memory chip that resides on the sensor. The monitor reads the calibration data when each sensor is plugged in and uses it to normalize the sensor signals. Each sensor is calibrated by using an optical fixture to measure the efficiency of all signals monitored. Accurate and repeatable placement of each sensor on the optical fixture is used to optimize the accuracy of the calibration. This accurate placement is achieved using locating pins (not shown) on the optical fixture and corresponding locating holes 40 on the flexcircuit assembly. The location of the pins and holes are far enough apart that this relative positioning accuracy and repeatability is easily achieved from sensor to sensor.

Figure 7A:
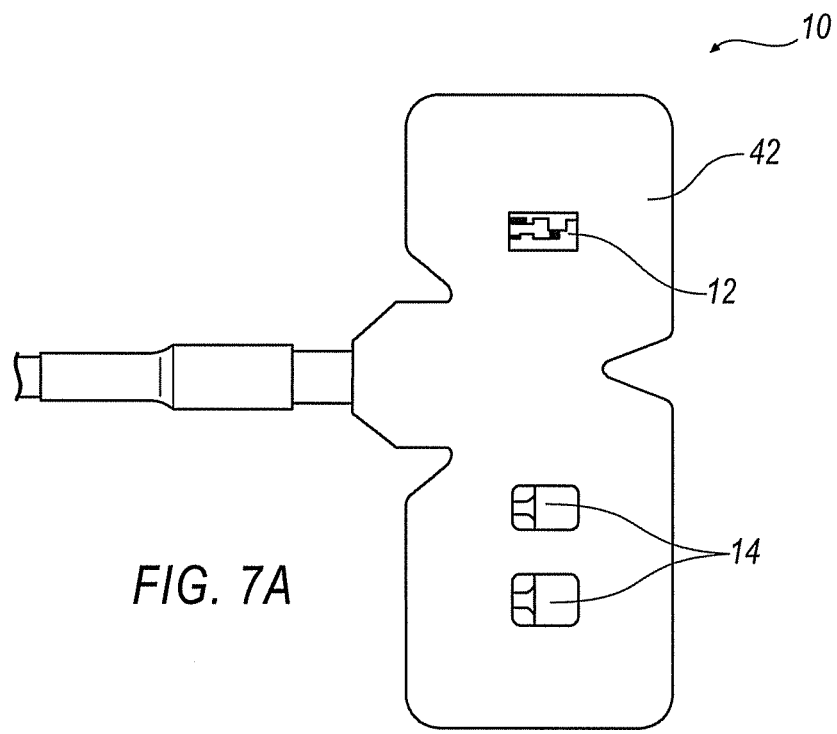
FIG. 7A illustrates a patient side view of an exemplary sensor pad assembly, according to an embodiment.
Figure 7B:
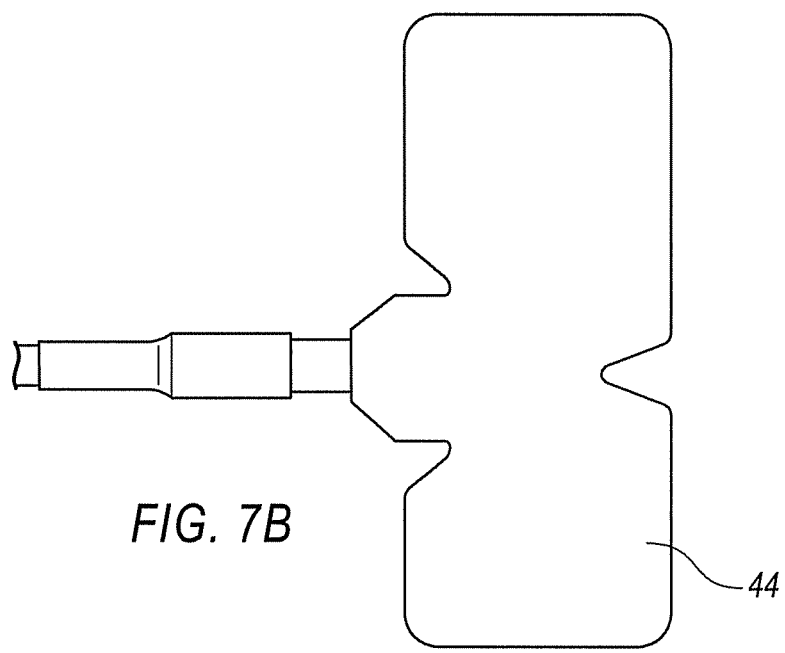
FIG. 7B illustrates a top side view of an exemplary sensor pad assembly, according to an embodiment.
Figure 7C:
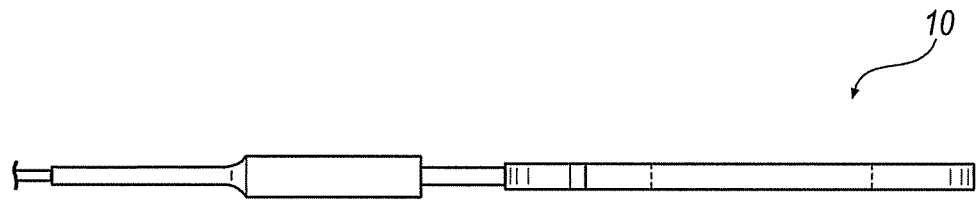
FIG. 7C illustrates a side view of an exemplary sensor pad assembly, according to an embodiment.
Figure 7D:
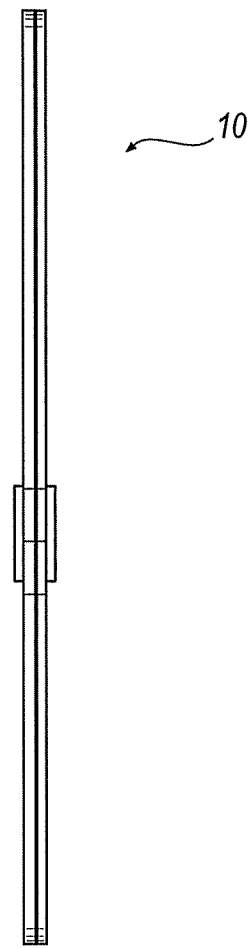
FIG. 7D illustrates another side view of an exemplary sensor pad assembly, according to an embodiment.

FIGS. 7A-7D illustrate a patient side, a top side, and two side views, respectively, of an exemplary sensor pad 10 as assembled according to FIGS. 1 and 2. The assembled sensor 10 is configured to deform to a shape approximating the smallest compound curvature of a human head. The assembled sensor 10 retains its shape indefinitely with no external force or pressure, it minimizes potential pressure points, it is easily applied to and removed from delicate patient skin and it can be calibrated accurately and repeatibly. The sensor has the capability of conforming to the relatively small radius compound curvature of neonates for cerebral and somatic applications and can also be used to enhance pediatric and adult applications. As shown in FIGS. 7C and 7D, the sensor pad assembly 10 has uniform patient side 47 and top side 44 surfaces that minimize potential pressure points. In other words, the sensor pad assembly 10 has an overall uniform thickness with no protrusions on either side of the sensor pad.

It is to be understood that the above description is intended to be illustrative and not restrictive. Many alternative approaches or applications other than the examples provided would be apparent to those of skill in the art upon reading the above description. The scope of the invention should be determined, not with reference to the above description, but should instead be determined with reference to the appended claims, along with the full scope of equivalents to which such claims are entitled. It is anticipated and intended that future developments will occur in the arts discussed herein, and that the disclosed systems and methods will be incorporated into such future examples. In sum, it should be understood that the invention is capable of modification and variation and is limited only by the following claims.

The present embodiments have been particularly shown and described, which are merely illustrative of the best modes. It should be understood by those skilled in the art that various alternatives to the embodiments described herein may be employed in practicing the claims without departing from the spirit and scope as defined in the following claims. It is intended that the following claims define the scope of the invention and that the method and apparatus within the scope of these claims and their equivalents be covered thereby. This description should be understood to include all novel and non-obvious combinations of elements described herein, and claims may be presented in this or a later application to any novel and non-obvious combination of these elements. Moreover, the foregoing embodiments are illustrative, and no single feature or element is essential to all possible combinations that may be claimed in this or a later application.

All terms used in the claims are intended to be given their broadest reasonable constructions and their ordinary meanings as understood by those skilled in the art unless an explicit indication to the contrary is made herein. In particular, use of the singular articles such as "a," "the," "said," etc. should be read to recite one or more of the indicated elements unless a claim recites an explicit limitation to the contrary.

What is claimed is:

1. A sensor for measuring physiological characteristics, comprising:
   a circuit assembly having a plurality of optical components mounted on a flexible planar substrate; and
   a deformable material layer configured to deform as the sensor is applied to and conforms to a non-planar, compound curvature surface on the patient, wherein said deformable material causes the sensor to tend to maintain the conformed shape of the sensor independent of an external force;
   wherein a center horizontal plane of said flexible planar substrate is axially aligned with the mechanical center of said optical components.

2. The sensor of claim 1, wherein said deformable material is a metal layer in the sensor.

3. The sensor of claim 2, wherein said metal layer is an aluminum layer.

4. The sensor of claim 1, wherein said deformable material is integrated into said flexible planar substrate.

5. The sensor of claim 1, further comprising at least two planar material layers disposed on opposite parallel surfaces of said flexible planar substrate.

6. The sensor of claim 5, wherein said material layers are foam.

7. The sensor of claim 5, wherein a thickness of said two material layers collectively equal the thickness of said plurality of optical components.

8. The sensor of claim 1, wherein said optical components include at least one light emitter and at least one light detector.

9. The sensor of claim 1, further comprising an adhesive layer configured to adhere the sensor to a surface of the patient, and wherein said deformable material is configured to tend to maintain the conformed shape of the sensor independent of any adhesion force applied by said adhesive layer.

10. The sensor of claim 1, wherein said deformable material is configured to tend to maintain the conformed shape of the sensor after the sensor is removed from the patient.

11. A sensor for measuring physiological characteristics, comprising:
   a circuit assembly having a plurality of optical components mounted on a flexible planar substrate; and
   a deformable material layer configured to deform as the sensor is applied to and conforms to a non-planar, compound curvature surface on the patient, wherein said deformable material causes the sensor to tend to maintain the conformed shape of the sensor independent of an external force;
   wherein a center longitudinal axis of each said optical component is aligned with and coincides with a center horizontal plane of said flexible planar substrate.

12. The sensor of claim 11, wherein said deformable material is a metal layer in the sensor.

13. The sensor of claim 11, wherein said deformable material is integrated into said flexible planar substrate.

14. The sensor of claim 11, further comprising at least two planar material layers disposed on opposite major surfaces of said flexible planar substrate, wherein a thickness of said two material layers collectively equal the thickness of said plurality of optical components.

15. The sensor of claim 11, wherein said optical components include at least one light emitter and at least one light detector.

16. The sensor of claim 11, further comprising an adhesive layer configured to adhere the sensor to a surface of the patient, and wherein said deformable material is configured to tend to maintain the conformed shape of the sensor independent of any adhesion force applied by said adhesive layer.

17. The sensor of claim 11, wherein said deformable material is configured to tend to maintain the conformed shape of the sensor after the sensor is removed from the patient.

18. A sensor for measuring physiological characteristics, comprising:
   a circuit assembly having a plurality of optical components mounted on a flexible planar substrate; and
   a deformable material layer configured to deform as the sensor is applied to and conforms to a non-planar, compound curvature surface on the patient, wherein said deformable material causes the sensor to tend to maintain the conformed shape of the sensor independent of an external force;
   wherein said optical components are mounted such that half of each component mounted in said orifice extends above a center horizontal plane of said flexible planar substrate and the other half of each component mounted in said orifices extends below said center horizontal plane of said flexible planar substrate.

19. The sensor of claim 18, wherein said deformable material is a metal layer in the sensor.

20. The sensor of claim 18, wherein said deformable material is integrated into said flexible planar substrate.

21. The sensor of claim 18, further comprising at least two planar material layers disposed on opposite major surfaces of said flexible planar substrate, wherein a thickness of said two material layers collectively equal the thickness of said plurality of optical components.

22. The sensor of claim 18, wherein said optical components include at least one light emitter and at least one light detector.

23. The sensor of claim 18, further comprising an adhesive layer configured to adhere the sensor to a surface of the patient, and wherein said deformable material is configured to tend to maintain the conformed shape of the sensor independent of any adhesion force applied by said adhesive layer.

24. The sensor of claim 18, wherein said deformable material is configured to tend to maintain the conformed shape of the sensor after the sensor is removed from the patient.

* * * * *